US012584108B2

(12) United States Patent
Wang et al.

(10) Patent No.: US 12,584,108 B2
(45) Date of Patent: Mar. 24, 2026

(54) METHOD FOR SEPARATING MIGRASOMES FROM MACROPHAGES

(71) Applicant: Affiliated Hospital of Jiangsu University, Zhenjiang (CN)

(72) Inventors: Xuefeng Wang, Zhenjiang (CN); Yongbin Ma, Zhenjiang (CN); Shang Wang, Zhenjiang (CN)

(73) Assignee: Affiliated Hospital of Jiangsu University, Zhenjiang (CN)

( * ) Notice: Subject to any disclaimer, the term of this patent is extended or adjusted under 35 U.S.C. 154(b) by 313 days.

(21) Appl. No.: 18/402,999

(22) Filed: Jan. 3, 2024

(65) Prior Publication Data

US 2024/0336894 A1 Oct. 10, 2024

(30) Foreign Application Priority Data

Apr. 4, 2023 (CN) .......................... 202310349563.0

(51) Int. Cl.
| | |
|---|---|
| *C12N 5/0786* | (2010.01) |
| *C23C 14/14* | (2006.01) |
| *C23C 14/20* | (2006.01) |

(52) U.S. Cl.
CPC ............ *C12N 5/0645* (2013.01); *C23C 14/14* (2013.01); *C23C 14/205* (2013.01); *C12N 2500/02* (2013.01); *C12N 2500/05* (2013.01); *C12N 2500/30* (2013.01); *C12N 2500/84* (2013.01); *C12N 2509/00* (2013.01); *C12N 2523/00* (2013.01); *C12N 2527/00* (2013.01); *C12N 2529/00* (2013.01)

(58) Field of Classification Search
CPC .............. C12N 5/0645; C12N 2500/02; C12N 2500/05; C12N 2500/30; C12N 2500/84; C12N 2509/00; C12N 2523/00; C12N 2527/00; C12N 2529/00; C23C 14/14; C23C 14/205
See application file for complete search history.

(56) References Cited

PUBLICATIONS

CNIPA, Notification of First Office Action for CN202310349563.0, Jul. 25, 2025.
Affiliated Hospital of Jiangsu University (Applicant), Replacement claims (allowed) of CN202310349563.0, Aug. 13, 2025.
CNIPA, Notification to grant patent right for invention in CN202310349563.0, Aug. 27, 2025.

*Primary Examiner* — Michael A Band
(74) *Attorney, Agent, or Firm* — COOPER LEGAL GROUP LLC

(57) ABSTRACT

A simple and efficient method for separating migrasomes from macrophages is provided. The method separates migrasomes having a diameter range of 0.5 micrometers ($\mu$m) to 3 $\mu$m by intercepting through a filter and eluting through reverse filtration successfully. The separated migrasome has a vesicle-liked structure and wrinkles on its surface, and the separated migrasome has a diameter over 500 nanometers (nm). The separated migrasomes express their characteristic proteins PIGK, EOGT, and TSPAN4, but do not express specific markers TSG101 and ALIX of EVs, indicating that the separated migrasomes are a unique type of vesicles distinct from extracellular vesicles (EVs). The integrity of ribonucleic acids (RNA) carried by the migrasomes is not affected. The method for separating migrasomes from macrophages has the characteristics of simplicity, high efficiency, good controllability, good repeatability, and low cost, and large special equipment is not needed.

4 Claims, 2 Drawing Sheets

METHOD FOR SEPARATING MIGRASOMES FROM MACROPHAGES

TECHNICAL FIELD

The disclosure relates to the technical field of biomedicine, and particularly to a simple and efficient method for separating migrasomes from macrophages.

BACKGROUND

Extracellular vesicles (EVs) involved in various pathological and physiological processes have rapidly developed as intercellular communication tools. For example, proteins, nucleic acids, various cytokines and growth factors contained in EVs mediate immune regulation, angiogenesis, tumor growth, damage repair, etc. Therefore, EVs can be used in diagnosis, treatment, and prognosis evaluation of various diseases. Migrasome is a new and unique type of vesicle secreted and released by cells during cell migration, with a particle size in a range of 0.5 micrometers ($\mu$m) to 3 $\mu$m. It has been confirmed that the migrasomes exist in various cells, tissues, and body fluids. Research has shown that the migrasomes are not only crucial for organ formation during embryonic development, but also serve as a functional way for cellular exocytosis of damaged mitochondria to maintain cellular homeostasis. In addition, the migrasomes not only participate in the progression of stroke (also referred to as cerebral apoplexy), but also serve as non-invasive biomarkers for renal podocyte injury. These evidences indicate that, similar to other EVs, the migrasomes also have great potentials and values in disease diagnosis, treatment, and prognosis evaluation. However, the current research on the migrasomes is still in its preliminary stage, especially in their functions. Efficient separation of the migrasomes is an important prerequisite for conducting their functional research.

At present, there are two methods for separating the migrasomes. One is to extract the migrasomes through low-speed stepwise centrifugation, but only a crude extract of the migrasomes is obtained. The other method is to use low-speed stepwise centrifugation firstly, use gradient density centrifugation later, and finally use ultra-high-speed centrifugation for separation and purification. The second method is currently the most reliable separation and purification method, but its operation steps are cumbersome, separation time is long, and equipment requirements are high, making it difficult to meet the needs of large-scale extraction and subsequent applications. Therefore, there is an urgent need to develop a new method for separating the migrasomes. The new method is of great significance to the research of biological functions of the migrasomes as new EVs and their important role as intercellular messengers for disease diagnosis and treatment.

SUMMARY

In order to solve one of the above-mentioned technical problems, the disclosure provides a simple and efficient method for separating migrasomes from macrophages. The disclosure separates the migrasomes having a diameter range of 0.5 micrometers ($\mu$m) to 3 $\mu$m by intercepting through a filter and eluting through reverse filtration, thereby realizing rapid separation of the migrasomes in macrophages.

To achieve the above purpose, the disclosure uses the following technical solutions:

a method for separating migrasomes from macrophages, including:

step 1, placing macrophages to be separated in Dulbecco's modified eagle medium (DMEM) containing fetal bovine serum for overnight routine culture;

step 2, placing sterile glass slides into a well plate to inoculate the macrophages after the overnight routine culture, adding a DMEM with extracellular vesicle (EV)-free serum into each well of the well plate, placing the well plate added with the DMEM with the extracellular vesicle (EV)-free serum into a saturated humidity incubator with 50 milliliters per liter (mL/L) $CO_2$ for culture at 37 Celsius degrees (° C.) for 24 hours to 36 hours; removing the supernatant in each well of the well plate, adding 2.5% glutaraldehyde to completely cover cell surfaces of the macrophages after culture and placing the covered macrophages into a refrigerator at 4° C. for overnight, and then removing the glutaraldehyde; rinsing the macrophages after removing the glutaraldehyde by using a phosphate buffer solution (PBS), and then fixing the rinsed macrophages for 1 hour to 2 hours by using a pre-cooled osmic acid solution; re-rinsing the fixed macrophages by using the PBS, and then performing stepwise dehydration on the re-rinsed macrophages by using alcohols to obtain dehydrated macrophages; drying the dehydrated macrophages by using a freeze dryer in vacuum to obtain dried macrophages; and spraying a gold coating on the dried macrophages by using an ion sputtering device to thereby determine morphology of the migrasomes of the macrophages;

step 3, inoculating the macrophages after the overnight routine culture in a cell culture dish after determining the morphology of the migrasomes of the macrophages, adding the DMEM with the EV-free serum into the cell culture dish, and placing the cell culture dish added with the DMEM with the EV-free serum into the saturated humidity incubator with 50 mL/L $CO_2$ for culture at 37° C. to obtain cultured macrophages; when a cell confluence rate of the macrophages reaches 40-50%, digesting the cultured macrophages using a trypsin to obtain a mixture, centrifuging the mixture to collect a supernatant of the mixture; filtering the supernatant with a filter to obtain intercepted migrasomes, and reversing a direction of the filter for reverse filtration to elute the intercepted migrasomes intercepted by the filter; ultrafiltering the eluted migrasomes using an ultrafiltration tube with a molecular weight cutoff of 100 kilodaltons (KD), thereby obtaining the migrasomes.

In an embodiment, in the step 2, concentrations of the alcohols used to perform the stepwise dehydration are 50%, 70%, 90%, 95%, and 100% respectively.

In an embodiment, in the step 2, a current of the ion sputtering device is 10 milliamperes (mA), and working time of the ion sputtering device is 120 seconds(s).

In an embodiment, in the step 3, the filter defines a filter hole configured to intercept the migrasomes with a diameter range of 0.5 micrometers ($\mu$m) to 3 $\mu$m.

In an embodiment, in the step 3, a diameter of the filter hole is 0.45 $\mu$m.

In an embodiment, in the step 3, the reversing a direction of the filter for reverse filtration includes: after reversing the direction of the filter, using a sterile silicone tube to physically connect the filter to a syringe containing a pre-cooled PBS, and then performing the reverse filtration.

In an embodiment, in the step 3, a diameter of the migrasomes is in a range of 0.5 μm to 3 μm.

The disclosure uses the filter to intercept the migrasomes and perform the reverse filtration to elute the migrasomes having the diameter range of 0.5 μm to 3 μm. The method for separating the migrasomes from the macrophages provided by the disclosure is a simple and efficient method. In the embodiment of the disclosure, multiple contraction filaments extend from a tail surface of RAW264.7 cell, with membranous vesicles at its tips or forks; and the membranous vesicles has a diameter in a range of 0.5 μm to 3 μm. The separated migrasome is circular in shape, the separated migrasome has a vesicle-liked structure and wrinkles on its surface, and the separated migrasome has a diameter over 500 nanometers (nm), which is basically consistent with the morphology and diameter results under scanning electron microscopy. The separated migrasomes express their characteristic proteins PIGK, EOGT, and TSPAN4, but do not express specific markers (TSG101 and ALIX) of EVs, indicating that the separated migrasomes are a unique type of vesicles distinct from EVs. The migrasomes separated by the disclosure will not affect the integrity of ribonucleic acids (RNA) carried by the migrasomes. The method for separating the migrasomes from the macrophages provided by the disclosure has the characteristics of simplicity, high efficiency, good controllability, good repeatability, and low cost, and large special equipment is not needed in the disclosure.

DETAILED DESCRIPTION OF EMBODIMENTS

Figure 1:
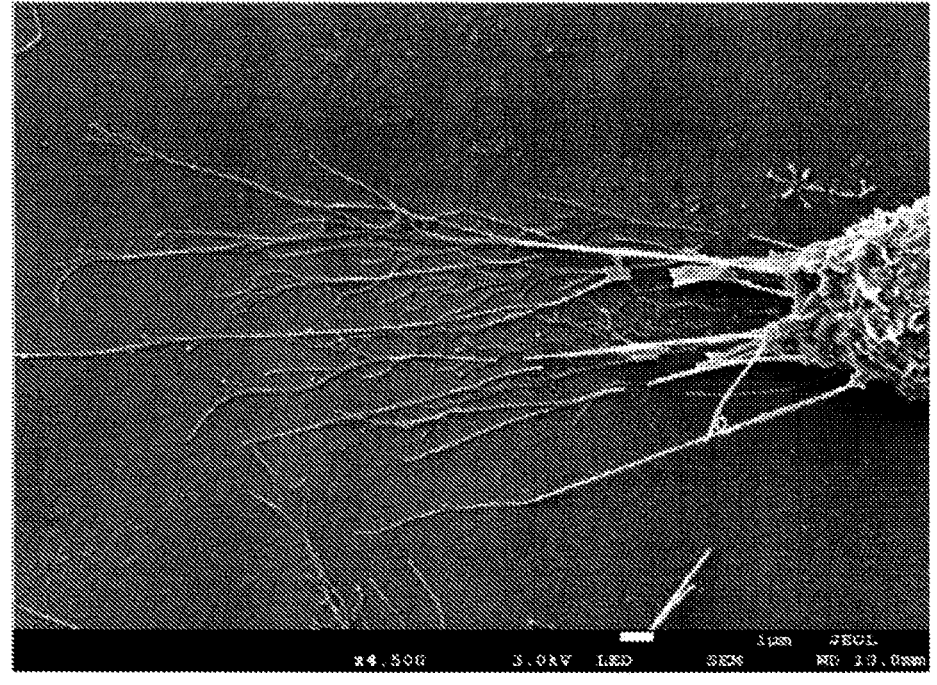
FIG. 1 illustrates a morphological characteristic diagram of migrasomes of macrophages observed by a scanning electron microscope (SEM).

The disclosure will be further described by the following embodiment, however, the scope of the disclosure is not limited to the following embodiment. Materials and test methods used in the tests are generally and/or specifically described. Test methods for which specific conditions are not described in the following embodiment are generally performed based on conventional conditions or conditions s recommended by manufacturers. Reagents, biomaterials and others used in the following embodiment are commercially available unless otherwise specified.

Embodiment 1

A method for separating migrasomes from macrophages provided by the disclosure includes the following steps.

Step 1: Culture of Macrophages.

In the step 1, specifically, RAW264.7 mouse macrophages are placed in Dulbecco's modified eagle medium (DMEM) containing fetal bovine serum with a concentration of 100 milliliters per liter (mL/L), and then the DMEM is placed into a saturated humidity incubator at 37 Celsius degrees (° C.) with 50 mL/L carbon dioxide ($CO_2$) for overnight routine culture.

Step 2: Observation of Migrasomes of RAW264.7 Macrophages Under a Scanning Electron Microscope (SEM).

In the step 2, specifically, sterile round glass slides are placed into a 24-well plate to inoculate the RAW264.7 macrophages, with $5\times10^4$ RAW264.7 macrophages per well. 2 mL DMEM with extracellular vesicle (EV)-free serum is added into each well, then the well plate is placed into the saturated humidity incubator to culture the RAW264.7 macrophages at 37° C. with 50 mL/L $CO_2$ for 24 hours. After removing a supernatant in each well, 25 mL/L (2.5%) glutaraldehyde is added to completely cover cell surfaces of the RAW264.7 macrophages, then the RAW264.7 macrophages are placed into a refrigerator at 4° C. for overnight. Then the glutaraldehyde in each well is removed, a phosphate buffer solution (PBS) is used to rinse the RAW264.7 macrophages twice, and the RAW264.7 macrophages are rinsed by the PBS for 10 minutes (min) each time. After removing the PBS, 10 mL/L pre-cooled osmic acid solution is used to fix the RAW264.7 macrophages for 1 hour, and the PBS is used to rinse the RAW264.7 macrophages twice again. Then alcohols (concentrations of the alcohols are 50%, 70%, 90%, 95%, and 100% respectively) are used to perform stepwise dehydration twice on the RAW264.7 macrophages to obtain dehydrated RAW264.7 macrophages, and time for each stepwise dehydration is 15 min. After the above operations, a freeze dryer is used to dry the dehydrated RAW264.7 macrophages in vacuum to obtain dried RAW264.7 macrophages, and an ion sputtering device (a current of the ion sputtering device is 10 milliamperes (mA) and working time of the ion sputtering device is 120 seconds) is used to spray a gold coating on the dried RAW264.7 macrophages. A SEM is used to observe morphology of migrasomes of the coated RAW264.7 macrophages and take pictures. In this situation, the morphology of migrasomes of the RAW264.7 macrophages can be observed and determined for ensuring that the migrasomes can be obtained by the method of the disclosure.

FIG. 1 illustrates a morphological characteristic diagram of migrasomes of macrophages (i.e., the RAW264.7 macrophages) observed by SEM. As shown in FIG. 1, multiple contraction filaments extend from a tail surface of RAW264.7 macrophages, with membranous vesicles at its tips or forks; and each of the membranous vesicles has a diameter in a range of 0.5 micrometers (μm) to 3 μm.

Step 3: Separation of Migrasomes.

In the step 3, specifically, after the morphology of migrasomes of the dried RAW264.7 macrophages is determined and recorded. RAW264.7 macrophages after the overnight routine culture are inoculated in a 100 millimeters (mm) cell culture dish. 6 mL DMEM with EV-free serum is added into the cell culture dish, and the cell culture dish is placed into a saturated humidity incubator with 50 mL/L $CO_2$ for culture at 37° C. to obtain cultured macrophages. When a cell confluence rate of the macrophages reaches 40-50%, 2.5 g/L trypsin is used to digest the cultured macrophages to obtain a mixture, and the mixture is centrifuged at 4° C. for 10 min at 1000 gravity acceleration (g), thereby collecting a crude supernatant of the mixture. The crude supernatant is centrifuged at 4° C. for 20 min at 4000 g to remove cell debris and impurities, thereby collecting a supernatant of the mixture. The supernatant is filtered by a filter (a diameter of the filter hole of the filter is 0.45 μm) to obtain intercepted migrasomes (i.e., migrasomes intercepted by the filter). A direction of the filter is reversed, then a sterile silicone tube is used to physically connect the filter to a syringe containing 5 mL pre-cooled PBS, and then a reverse surface of the filter is used to perform reverse filtration and elute the intercepted migrasomes intercepted by the filter. After the intercepted migrasomes are eluted, an ultrafiltration tube with a molecular weight cutoff of 100 kilodaltons (KD) is used for ultrafiltration of the intercepted migrasomes, and a remaining liquid obtained after the ultrafiltration is the migrasomes (i.e., separated and purified migrasomes). The migrasomes are packaged in eppendorf (EP) tubes. The EP tubes are stored in a refrigerator at −80° C. for subsequent use.

Figure 2:
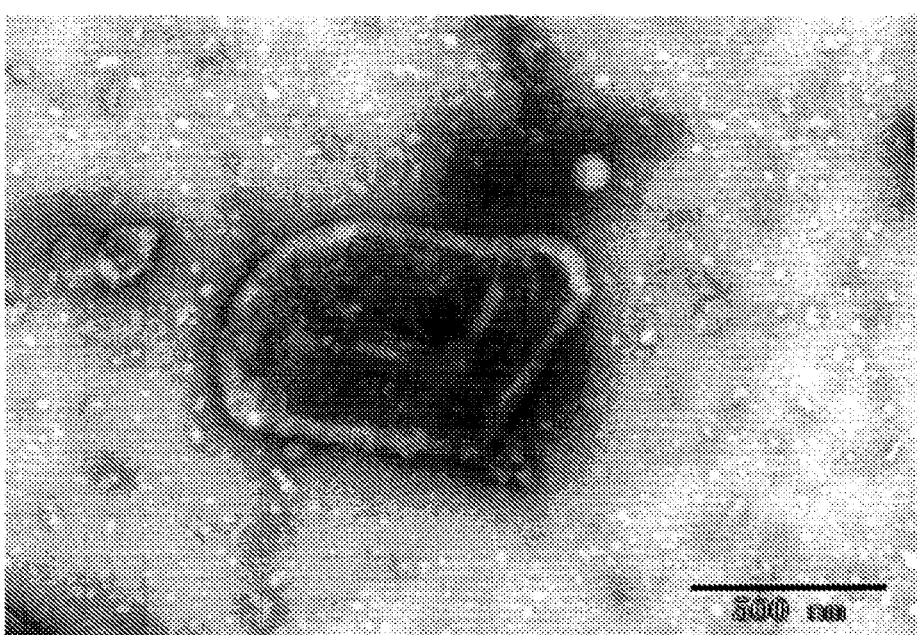
FIG. 2 illustrates a morphological characteristic diagram of a migrasome separated from macrophages observed by transmission electron microscope (TEM).

20 microliters (μL) separated and purified migrasomes obtained in the embodiment 1 are taken and mixed evenly, then dropwise added onto a sample carrying copper mesh, and let them stand at a room temperature for 1 min. Then a filter paper is used to remove the liquid from an edge of the copper mesh. 30 g/L phosphotungstic acid solution is dropwise added onto the copper mesh and negatively stain the migrasomes at the room temperature for 5 min. After the copper mesh is dried under an incandescent lamp, the copper mesh is placed in an electron microscope sample room to observe the morphology of the migrasomes under a transmission electron microscopy and take pictures. FIG. 2 illustrates a morphological characteristic diagram of a migrasome separated from the macrophages observed by a transmission electron microscope (TEM). As shown in FIG. 2, the migrasome separated from RAW264.7 macrophages is circular in shape, with a vesicular-like structure and wrinkles on its surface, and the separated migrasome has a diameter over 500 nanometers (nm), which is basically consistent with the morphology and diameter results under scanning electron microscopy.

Figure 3:
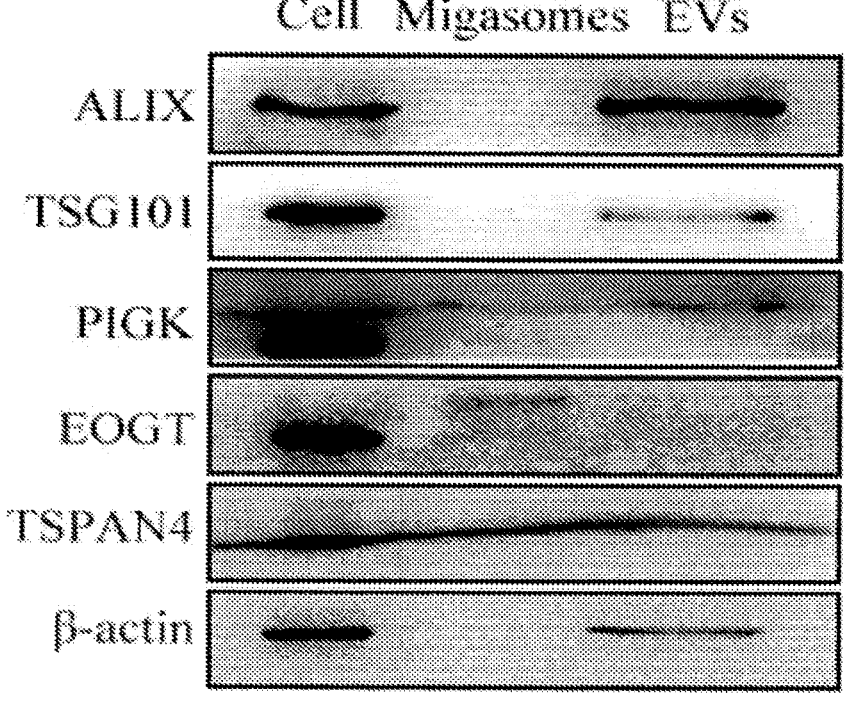
FIG. 3 illustrates a diagram showing expression of characteristic biomarkers of the migasomes detected by Western blot (WB).

The separated and purified migrasomes, EVs, and macrophages in the embodiment 1 are fully lysed respectively, and total proteins are collected and quantified using a bicinchoninic acid assay (BCA) protein assay kit. 60 micrograms (μg) protein sample of the total proteins is subjected to sodium dodecyl sulphate-polyacrylamide gel electrophoresis (SDS-PAGE) to electrotransfer to a polyvinylidene fluoride (PVDF) membrane, 50 g/L skimmed milk powder is added for blocking for 1 hour at the room temperature, and TSG101 antibody, ALIX antibody, PIGK antibody, EOGT antibody, TSPAN4 β-actin antibody (1:1000) are added at 4° C. for overnight. After Tris-buffered saline with Tween® 20 Detergent (TBST) washing, secondary horseradish peroxidase (HRP) labeled sheep anti-rabbit antibody (1:2000) is added to the protein sample for incubating at the room temperature for 1 hour. After TBST washing, a chemiluminescent substrate is added for color development, and an electrochemiluminescence (ECL) system is used for photo analysis. FIG. 3 illustrates a diagram showing expression of characteristic biomarkers of the migasomes detected by Western blot (WB). As shown in FIG. 3, the separated migrasomes express their characteristic proteins PIGK, EOGT, and TSPAN4, but do not express specific markers TSG101 and ALIX of EVs, indicating that the separated migrasomes are a unique type of vesicles distinct from EVs.

Figure 4:
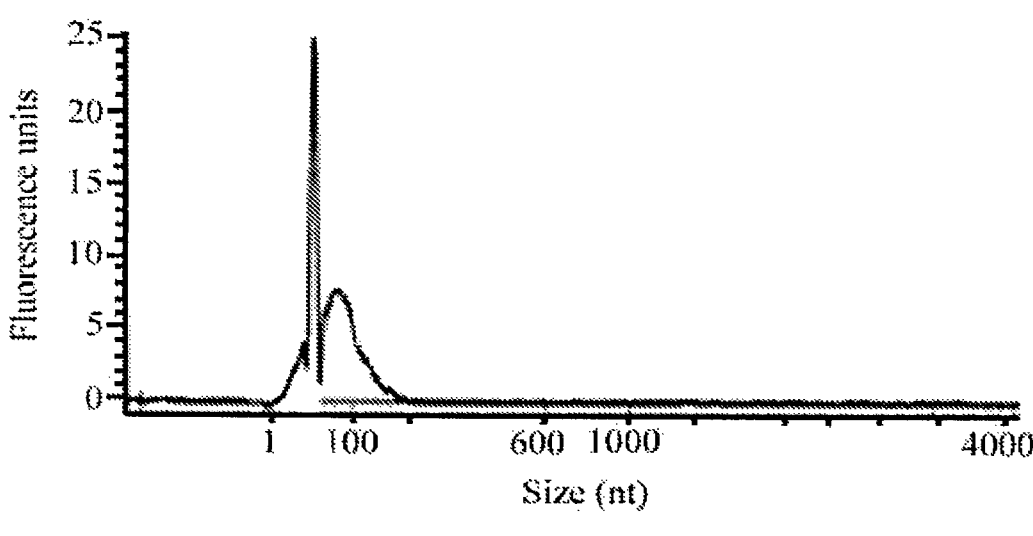
FIG. 4 illustrates a small ribonucleic acid (RNA) diagram of the migrasomes separated from the macrophages.

Ribonucleic acids (RNAs) are extracted and purified from the separated migrasomes, and then the total amount of RNAs is analyzed using a Labchip® bioanalyzer. RNA quantitative detection is performed by Hangzhou Lianchuan Biotechnology Co., Ltd., and all operating procedures are performed according to the recommended steps of the reagent kit. FIG. 4 illustrates a small RNA diagram of the migrasomes separated from macrophages. As shown in FIG.

4, the migrasomes produce a good small RNA electrophoresis peak with a length range of 25 nucleotides (nt) to 200 nt.

Therefore, the method of disclosure for separating and extracting the migrasomes can successfully separate the migrasomes from the macrophages, and the integrity of the RNAs carried by the migrator is not affected.

Although the embodiment of the disclosure has been shown and described above, it can be understood that the above embodiment is exemplary and cannot be understood as a limitation to the disclosure. Without contradiction, those skilled in the art may combine the different embodiments or examples described in this specification, as well as the features of different embodiments or examples.

What is claimed is:

1. A method for separating migrasomes from macrophages, comprising:

step 1, placing macrophages to be separated in a Dulbecco's modified eagle medium (DMEM) containing fetal bovine serum for overnight routine culture;

step 2, placing sterile glass slides into a well plate to inoculate the macrophages after the overnight routine culture, adding a DMEM with extracellular vesicle (EV)-free serum into each well of the well plate, placing the well plate added with the DMEM with the extracellular vesicle (EV)-free serum into a saturated humidity incubator with 50 milliliters per liter (mL/L) carbon dioxide ($CO_2$) for culture at 37 Celsius degrees (° C.) for 24 hours to 36 hours; removing a supernatant in each well of the well plate, adding 2.5% glutaraldehyde to completely cover cell surfaces of the macrophages after culture and placing the covered macrophages into a refrigerator at 4° C. for overnight, and then removing the glutaraldehyde; rinsing the macrophages after removing the glutaraldehyde by using a phosphate buffer solution (PBS), and then fixing the rinsed macrophages for 1 hour to 2 hours by using a pre-cooled osmic acid solution; re-rinsing the fixed macrophages by using the PBS, and then performing stepwise dehydration on the re-rinsed macrophages by using alcohols to obtain dehydrated macrophages; drying the dehydrated macrophages by using a freeze dryer in vacuum to obtain dried macrophages; and spraying a gold coating on the dried macrophages by using an ion sputtering device to obtain treated macrophages; and step 3, inoculating the treated macrophages obtained in the step 2 in a cell culture dish after, adding the DMEM with the EV-free serum into the cell culture dish, and placing the cell culture dish added with the DMEM with the EV-free serum into the saturated humidity incubator with 50 mL/L $CO_2$ for culture at 37° C. to obtain cultured macrophages; when a cell confluence rate of the macrophages reaches 40-50%, digesting the cultured macrophages using a trypsin to obtain a mixture, centrifuging the mixture to collect a supernatant of the mixture; filtering the supernatant with a filter having a pore size of 0.45 micrometers (μm) to obtain intercepted migrasomes, and reversing a direction of the filter for reverse filtration to elute the intercepted migrasomes intercepted by the filter; ultrafiltering the eluted migrasomes using an ultrafiltration tube with a molecular weight cutoff of 100 kilodaltons (KD), thereby obtaining remaining liquid as migrasomes;

wherein the reversing a direction of the filter for reverse filtration comprises: after reversing the direction of the filter, using a sterile silicone tube to physically connect the filter to a syringe containing a pre-cooled PBS, and then performing the reverse filtration.

2. The method as claimed in claim 1, wherein in the step 2, concentrations of the alcohols used to perform the step-wise dehydration are 50%, 70%, 90%, 95%, and 100% respectively.

3. The method as claimed in claim 1, wherein in the step 2, a current of the ion sputtering device is 10 milliamperes (mA), and working time of the ion sputtering device is 120 seconds(s).

4. The method as claimed in claim 1, wherein in the step 3, a diameter of the migrasomes is in a range of 0.5 μm to 3 μm.

\* \* \* \* \*